United States Patent
Imai

(10) Patent No.: US 10,568,498 B2
(45) Date of Patent: Feb. 25, 2020

(54) IMAGING UNIT AND ENDOSCOPE

(71) Applicant: OLYMPUS CORPORATION, Tokyo (JP)

(72) Inventor: Kenichi Imai, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 39 days.

(21) Appl. No.: 16/056,799

(22) Filed: Aug. 7, 2018

(65) Prior Publication Data
US 2018/0344139 A1    Dec. 6, 2018

Related U.S. Application Data

(63) Continuation of application No. PCT/JP2017/022057, filed on Jun. 15, 2017.

(30) Foreign Application Priority Data

Jun. 29, 2016 (JP) .................. 2016-129320

(51) Int. Cl.
| | | |
|---|---|---|
| *A61B 1/05* | (2006.01) | |
| *G02B 23/24* | (2006.01) | |
| *A61B 1/00* | (2006.01) | |
| *H01L 27/146* | (2006.01) | |

(52) U.S. Cl.
CPC ............ *A61B 1/051* (2013.01); *A61B 1/0011* (2013.01); *G02B 23/24* (2013.01); *H01L 27/14618* (2013.01)

(58) Field of Classification Search
CPC combination set(s) only.
See application file for complete search history.

(56) References Cited

U.S. PATENT DOCUMENTS

| | | |
|---|---|---|
| 2016/0367122 A1 | 12/2016 | Ichimura et al. |
| 2017/0035279 A1 | 2/2017 | Fujii |
| 2019/0167069 A1* | 6/2019 | Levy ................ A61B 1/015 |

FOREIGN PATENT DOCUMENTS

| | | |
|---|---|---|
| JP | H04-317280 A | 11/1992 |
| JP | H08-106055 A | 4/1996 |
| WO | WO 2016/042804 A1 | 3/2016 |
| WO | WO 2016/063603 A1 | 4/2016 |

OTHER PUBLICATIONS

International Search Report dated Aug. 8, 2017 issued in PCT/JP2017/022057.

* cited by examiner

*Primary Examiner* — Janese Duley
(74) *Attorney, Agent, or Firm* — Scully, Scott, Murphy & Presser, P.C.

(57) ABSTRACT

An imaging unit includes: an optical system configured to collect light; a semiconductor package including an image sensor and a sensor electrode; a plurality of electronic components; and a circuit board including: a first connection electrode provided on a front surface side of the circuit board; and an electronic component mounting area and an inspection electrode disposing area that are provided on a back surface side of the circuit board. A wall portion having a height higher than a height of the plurality of electronic components is formed at least on two facing sides around the electronic component mounting area, and a maximum thickness of the circuit board at the inspection electrode disposing area is thinner than a thickness of the circuit board including the wall portion, at the electronic component mounting area.

5 Claims, 8 Drawing Sheets

IMAGING UNIT AND ENDOSCOPE

CROSS-REFERENCE TO RELATED APPLICATION

This application is a continuation of PCT International Application No. PCT/JP2017/022057 filed on Jun. 15, 2017 which claims the benefit of priority from Japanese Patent Application No. 2016-129320 filed on Jun. 29, 2016, the entire contents of which are incorporated herein by reference.

BACKGROUND

1. Technical Field

The present disclosure relates to an imaging unit provided at a distal end of an insertion portion of an endoscope to be inserted into a subject and images the inside of the subject, and an endoscope.

2. Related Art

In the related art, endoscope apparatuses are widely used for various examination in the medical field and the industrial field. From among those endoscope apparatuses, endoscope apparatuses for medical use are capable of obtaining an in-vivo image inside a body cavity without the need of making an incision on a subject by inserting an elongated flexible insertion portion provided with an image sensor at a distal end thereof into the body cavity of a patient or the like, and is also capable of performing therapeutic treatment with a treatment tool projected from the distal end of the insertion portion as necessary, whereby the endoscope apparatuses for medical use are widely used.

At a distal end of an insertion portion of such an endoscope apparatus, an imaging unit including a circuit board on which electronic components, such as a capacitor and an IC chip, constituting a driving circuit of the image sensor are mounted is embedded (see JP H08-106055 A, for example).

SUMMARY

In some embodiments, an imaging unit includes: an optical system configured to collect light; a semiconductor package including an image sensor provided on a front surface side of the semiconductor package and a sensor electrode provided on a back surface side of the semiconductor package, the image sensor being configured to receive light made incident from the optical system and perform a photoelectric conversion to generates an electric signal; a plurality of electronic components; and a circuit board including: a first connection electrode that is provided on a front surface side of the circuit board; and an electronic component mounting area and an inspection electrode disposing area that are provided on a back surface side of the circuit board, the first connection electrode being connected to the sensor electrode of the semiconductor package, the electronic component mounting area including a second connection electrode to which the plurality of electronic components is connected, the inspection electrode disposing area including an inspection electrode. A wall portion having a height higher than a height of the plurality of electronic components is formed at least on two facing sides around the electronic component mounting area, and a maximum thickness of the circuit board at the inspection electrode disposing area is thinner than a thickness of the circuit board including the wall portion, at the electronic component mounting area.

In some embodiments, an endoscope includes: an insertion portion provided with the imaging unit at a distal end of the insertion portion.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
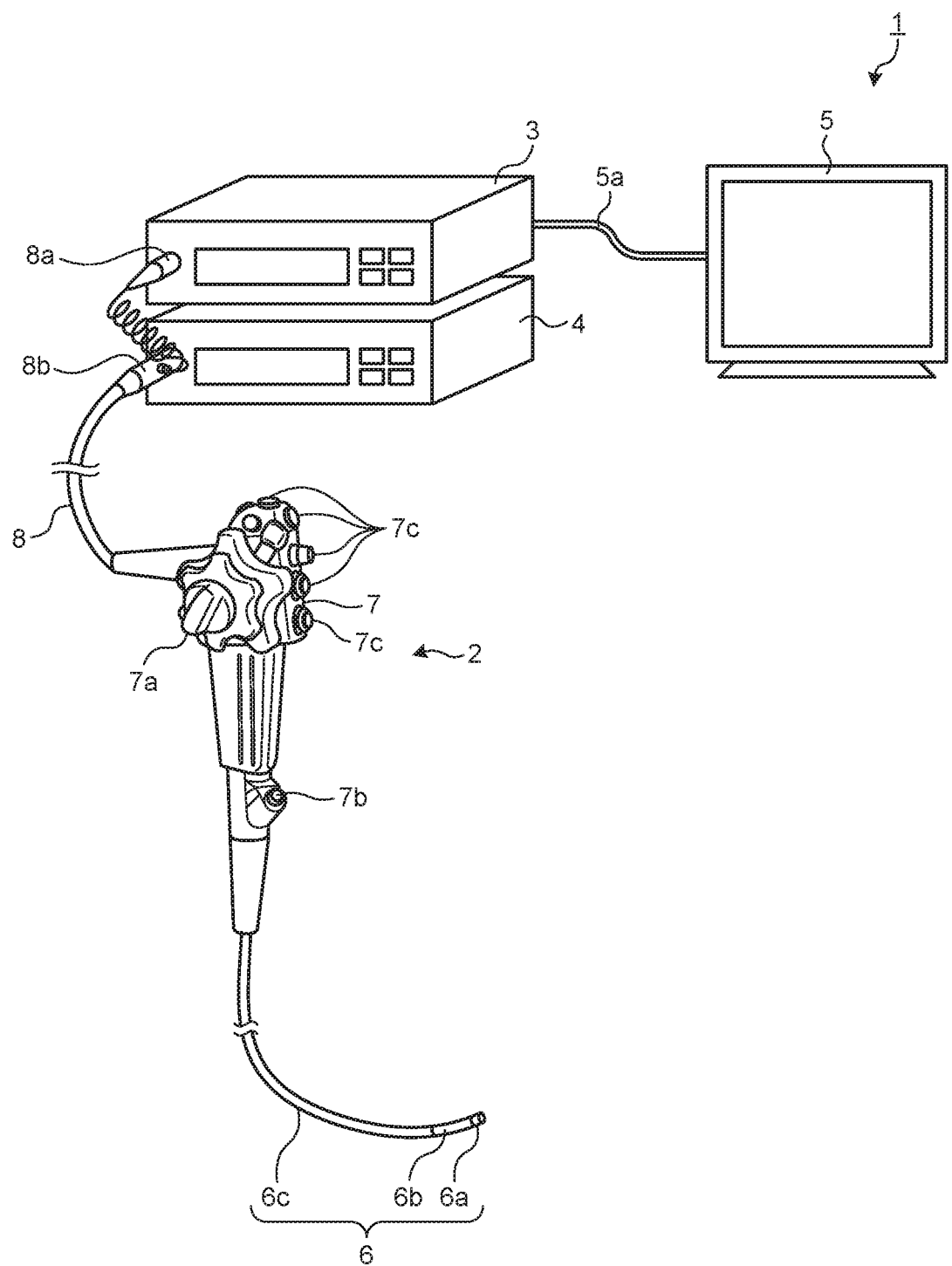
FIG. 1 is a diagram schematically illustrating an overall configuration of an endoscope system according to a first embodiment of the disclosure.

In the following descriptions, an endoscope system including an imaging unit will be described as a mode for carrying out the present invention (hereinafter referred to as "embodiment"). This invention is not limited by this embodiment. Further, the same portions are denoted by the same reference signs throughout the drawings. Note that the drawings are illustrative only, and a relationship between a thickness and a width of each member, a ratio of each member, and the like are different from reality. Besides, in the drawings, portions having dimensions and ratios different from each other are included.

First Embodiment

FIG. 1 is a diagram schematically illustrating an overall configuration of an endoscope system according to a first embodiment of the disclosure. As illustrated in FIG. 1, an endoscope system 1 according to the first embodiment includes an endoscope 2 to be inserted into a subject that images the inside of the subject and generates an image signal of the inside of the subject, an information processing apparatus 3 that performs predetermined image processing on the image signal captured by the endoscope 2 and controls each part of the endoscope system 1, a light source device 4 that generates illumination light of the endoscope 2, and a display device 5 that displays an image of the image signal having been subject to the image processing performed by the information processing apparatus 3.

The endoscope 2 includes an insertion portion 6 to be inserted into the subject, an operating unit 7 to be held by an operator, which is on a proximal end portion side of the insertion portion 6, and a flexible universal cord 8 extended from the operating unit 7.

The insertion portion 6 is formed using a lighting fiber (light guide cable), an electric cable, an optical fiber, and the like. The insertion portion 6 includes a distal end portion 6a incorporating an imaging unit to be described later, a bendable bend portion 6b including a plurality of bend pieces, and a flexible tube portion 6c provided on a proximal end portion side of the bend portion 6b, which is flexible. The distal end portion 6a is provided with an illumination unit that illuminates the inside of the subject via an illumination lens, an observation unit that images the inside of the subject, an aperture that communicates with a treatment tool channel, and an air/water supply nozzle (not illustrated).

The operating unit 7 includes a bend knob 7a for bending the bend portion 6b in the up and down direction and the right and left direction, a treatment tool insertion portion 7b through which a treatment tool such as medical forceps and a laser scalpel is inserted into a body cavity of the subject, and a plurality of switches 7c for operating a peripheral device such as the information processing apparatus 3, the light source device 4, an air supply device, a water supply device, and a gas supply device. The treatment tool inserted from the treatment tool insertion portion 7b is exposed from the aperture of the distal end of the insertion portion 6 via the treatment tool channel provided inside.

The universal cord 8 includes a lighting fiber, a cable, and the like. The universal cord 8 is branched at the proximal end thereof. One end of the branched ends is a connector 8a, and the other proximal end of the branched ends is a connector 8b. The connector 8a is attachable/detachable to/from a connector of the information processing apparatus 3. The connector 8b is attachable/detachable to/from the light source device 4. The universal cord 8 propagates the illumination light emitted from the light source device 4 to the distal end portion 6a via the connector 8b and the lighting fiber. Further, the universal cord 8 transmits an image signal captured by the imaging unit to be described later to the information processing apparatus 3 via the cable and the connector 8a.

The information processing apparatus 3 executes predetermined image processing on the image signal output from the connector 8a, and controls the entire endoscope system 1.

The light source device 4 includes a light source that emits light, a condenser lens, and the like. Under the control of the information processing apparatus 3, the light source device 4 emits light from the light source thereof, and supplies the light to the endoscope 2 connected via the connector 8b and the lighting fiber of the universal cord 8 as illumination light for the inside of the subject as an object.

The display device 5 includes, for example, a display using a liquid crystal, an organic electro luminescence (EL), or the like. The display device 5 displays various kinds of information including the image having been subject to predetermined image processing by the information processing apparatus 3 via a video cable 5a. This allows an operator to observe and determine behavior of the desired position inside the subject by operating the endoscope 2 while watching the image (in-vivo image) displayed by the display device 5.

Figure 2:
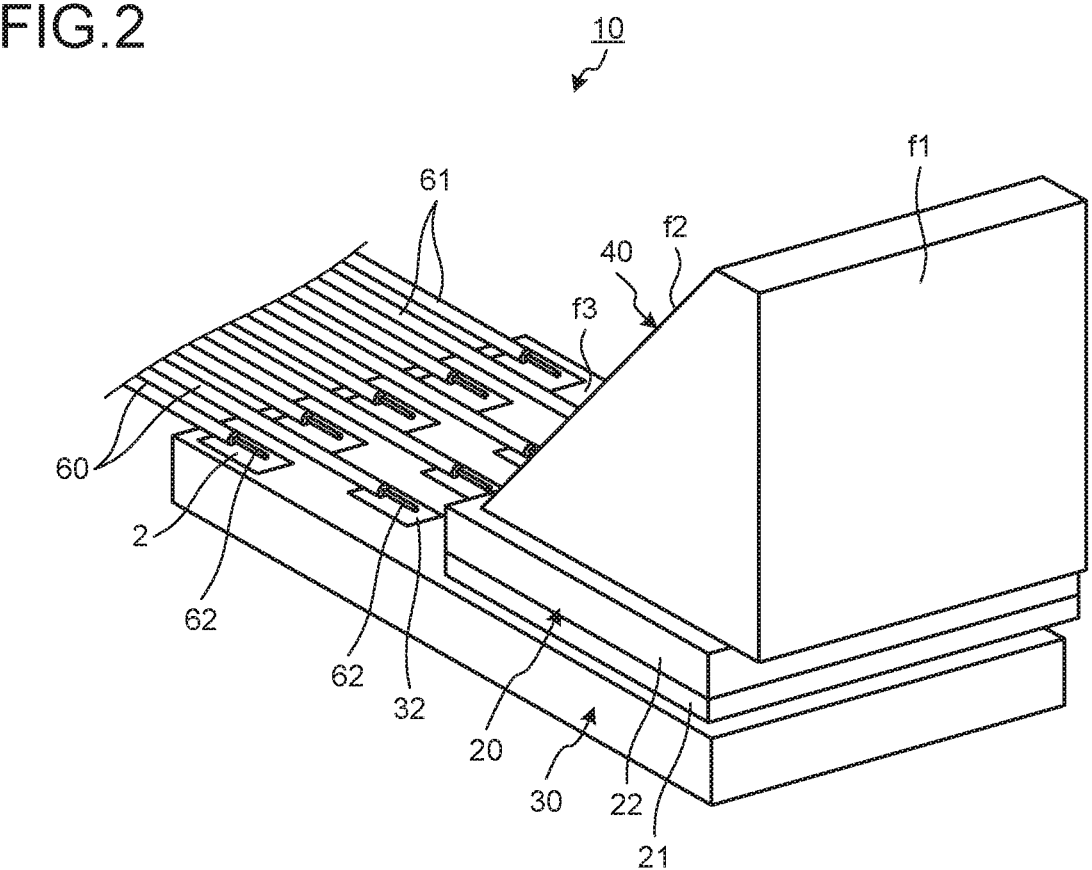
FIG. 2 is a perspective view of an imaging unit to be disposed at a distal end portion of the endoscope illustrated in FIG. 1.
Figure 3:
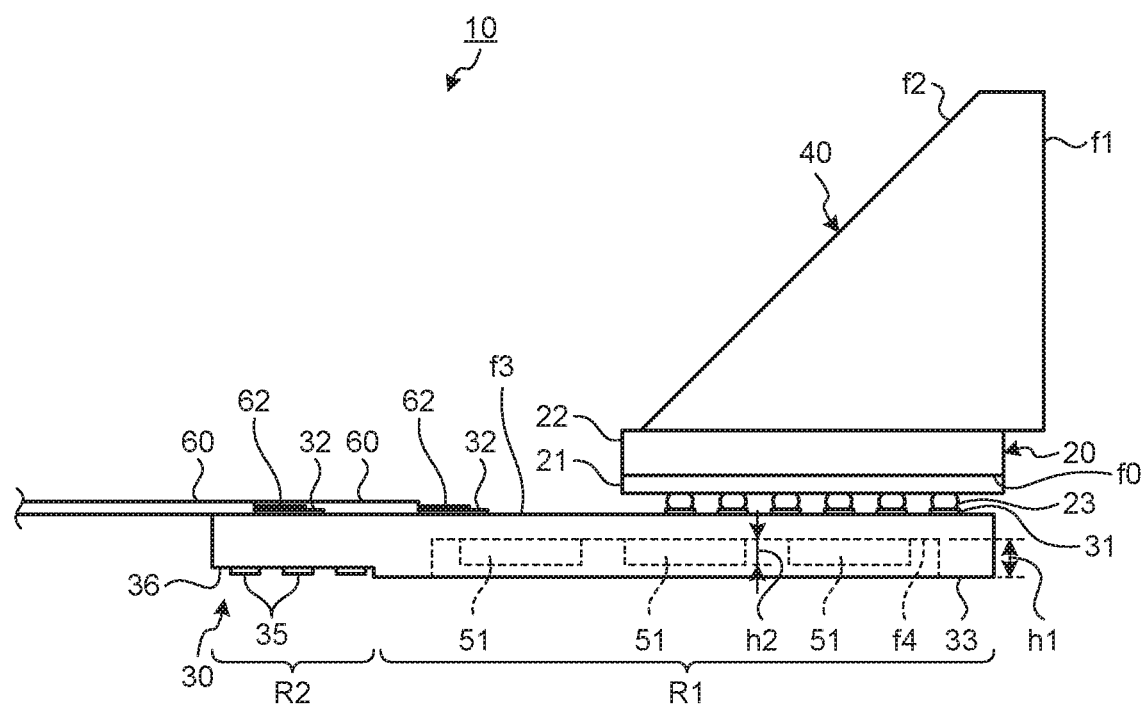
FIG. 3 is a side view of the imaging unit illustrated in FIG. 2.
Figure 4:
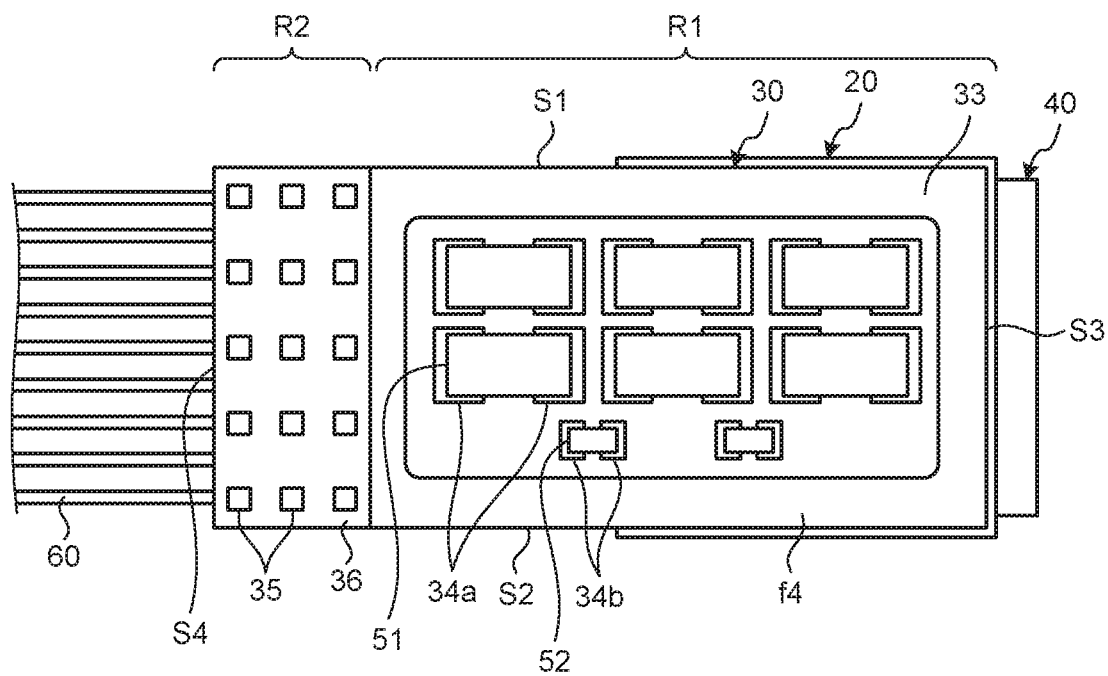
FIG. 4 is a bottom plan view of the imaging unit illustrated in FIG. 2.
Figure 5:
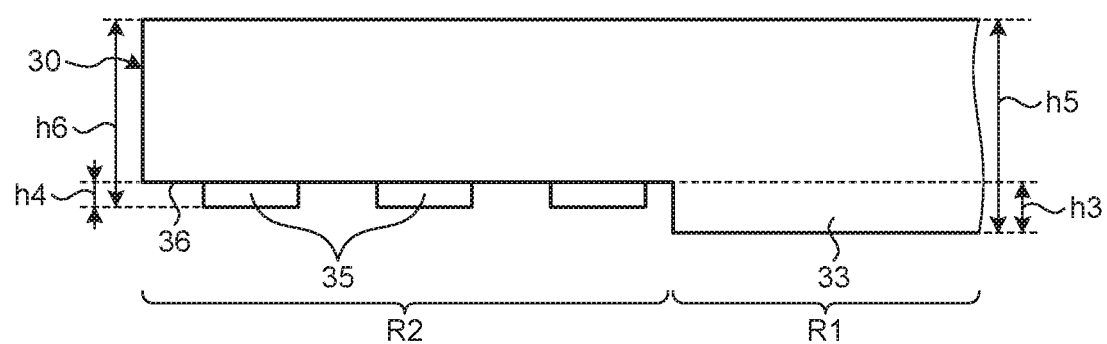
FIG. 5 is a partially enlarged side view illustrating the vicinity of a circuit board of the imaging unit in FIG. 2.

Next, an imaging unit 10 to be used in the endoscope system 1 will be described in detail. FIG. 2 is a perspective view of the imaging unit 10 to be disposed at the distal end portion 6a of the endoscope 2 illustrated in FIG. 1. FIG. 3 is a side view of the imaging unit 10 illustrated in FIG. 2. FIG. 4 is a bottom plan view of the imaging unit 10 illustrated in FIG. 2. FIG. 5 is a partially enlarged side view illustrating the vicinity of a circuit board of the imaging unit 10 in FIG. 2. Note that, in FIGS. 2 to 5, an underfill agent filled between a semiconductor package 20 and a circuit board 30, and a solder used for connecting a cable 60 and electronic components 51 and 52 are not illustrated.

The imaging unit 10 includes a prism 40 that collects and reflects incident light, the semiconductor package 20, a plurality of cables 60 that transmits an image signal from an image sensor 21 or supplies a power supply voltage, a plurality of electronic components 51 and 52, and the circuit board 30. The semiconductor package 20 includes the image sensor 21 that generates an electric signal by receiving light made incident from the prism 40 and performing a photoelectric conversion, and a connection electrode is formed on a back surface thereof. A first connection electrode 31 in a rectangular plate shape having a front surface f3 onto which the image sensor 21 is mounted and a cable connection electrode 32 to which the cable 60 is connected are disposed side by side on the circuit board 30, and second connection electrodes 34a and 34b onto which the electronic components 51 and 52 are mounted are formed on a back surface f4 of the circuit board 30.

The semiconductor package 20 has a structure in which a glass 22 is attached to the image sensor 21. The light made incident from a surface f1 of the prism 40 and reflected by a surface f2 is made incident to, via the glass 22, a surface f0 (light receiving surface) of the image sensor 21 having a light receiving section. A sensor electrode (not illustrated), and a bump 23 including a solder and the like are formed on a back surface of the light receiving surface of the image sensor 21. In the semiconductor package 20, wiring, electrode forming, resin sealing, and dicing are performed on an image sensor chip in a wafer state, and it is preferable that the semiconductor package 20 is ultimately a chip size package (CSP) in which the size of the image sensor chip directly becomes the size of the semiconductor package. Moreover, the semiconductor package 20 is what is called a horizontal installation type in which the surface f0 as a light receiving surface of the image sensor 21 is horizontally placed.

As the circuit board 30, a ceramic substrate, a glass epoxy substrate, a glass substrate, a silicon substrate, and the like are used. From the viewpoint of improving the reliability of the connection with the semiconductor package 20, it is preferable to use a component formed of a material having a thermal expansion coefficient similar to that of the material of the semiconductor package 20, that is, for example, a silicon substrate or a ceramic substrate.

On the front surface f3 of the circuit board 30, the first connection electrode 31 onto which the image sensor 21 is mounted and the cable connection electrode 32 to which the cable 60 is connected are disposed side by side in a direction in which the cable 60 extends. The cable 60 includes a conductor 62, and a casing 61 made of an insulator coating the conductor 62. The casing 61 is peeled off at the end portion thereof to expose the conductor 62. The exposed conductor 62 is connected to the respective cable connection electrodes 32. The cable connection electrodes 32 are disposed in a hound's-tooth check pattern (zigzag pattern) in order to reduce a diameter of the imaging unit 10 while a mounting density of the cable 60 is improved.

An electronic component mounting area R1 onto which the electronic components 51 and 52 are mounted and an inspection electrode disposing area R2 on which an inspection electrode 35 is disposed are formed on the back surface f4 of the circuit board 30. The electronic components 51 and 52 are, for example, a passive component such as a capacitor and a resistance coil, and an active component such as a driver IC. The electronic component mounting area R1 is disposed on the distal end side of the distal end portion 6a, and the inspection electrode disposing area R2 is disposed on the proximal end side. In the electronic component mounting area R1, the second connection electrodes 34a and 34b onto which the electronic components 51 and 52 are respectively mounted are formed, and a wall portion 33 having a height h1 higher than a height h2 of the electronic components 51 and 52 is disposed in the periphery. Although the wall portion 33 is disposed on four sides to surround the electronic component mounting area R1 in the first embodiment, the wall portion 33 may be formed at least on two facing sides. Since the wall portion 33 having the height h1 higher than the height h2 of the electronic components 51 and 52 is formed around the electronic component mounting area R1, the imaging unit 10 can be kept horizontal without using a special jig or the like at the time of production.

The inspection electrode disposing area R2 on the proximal end side of the surface f4 of the circuit board 30 forms a stepped portion 36, and the inspection electrode 35 is formed on the stepped portion 36. A depth h3 of the stepped portion 36 from a top end of the wall portion 33 is set to be larger than a thickness h4 of the inspection electrode 35, that is, the maximum thickness h6 of the circuit board 30 at the inspection electrode disposing area R2 (thickness of the circuit board 30 at the inspection electrode disposing area R2+thickness h4 of the inspection electrode 35) is set to be thinner than a thickness h5 of the circuit board 30 including the wall portion 33 formed in the electronic component mounting area R1, at the electronic component mounting area R1.

Figure 6:
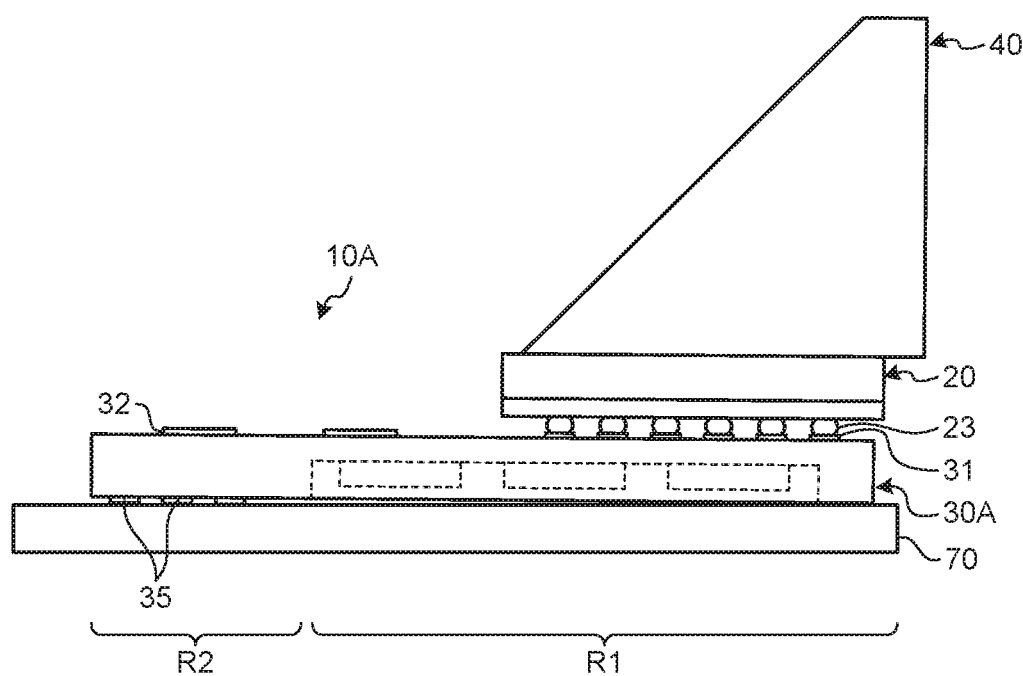
FIG. 6 is a side view of a conventional imaging unit.

FIG. 6 is a side view of a conventional imaging unit 10A. As illustrated in FIG. 6, in the imaging unit 10A, the wall portion 33 having a height higher than that of the electronic components 51 and 52 is formed around the electronic component mounting area R1, whereby a problem caused by protrusion of the upper surface of the electronic components 51 and 52 toward the back surface side of a circuit board 30A is overcome. However, it has been difficult to keep the imaging unit 10A horizontal due to the thickness of the inspection electrode 35. According to the first embodiment, the maximum thickness h6 of the circuit board 30 at the inspection electrode disposing area R2 is made thinner than the thickness h5 of the circuit board 30 including the wall portion 33 formed in the electronic component mounting area R1, at the electronic component mounting area R1, whereby the imaging unit 10 can be kept horizontal without using a special jig or the like at the time of production.

Moreover, in the process of manufacturing the imaging unit 10, quality of a connection can be inspected in each process by bringing a terminal of an inspection device into contact with the inspection electrode 35 after connecting the first connection electrode 31 of the circuit board 30 and the sensor electrode of the semiconductor package 20 using the bump 23, whereby a defective product can be found at an early state, and the production cost can be reduced.

Figure 7:
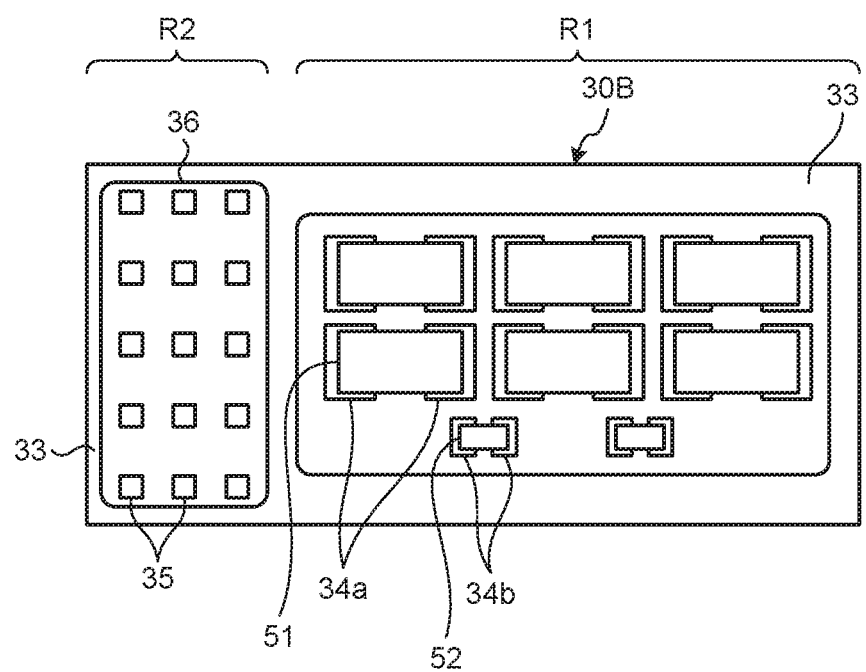
FIG. 7 is a bottom plan view of a circuit board according to a first variation of the first embodiment of the disclosure.

Although the wall portion 33 is formed only around the electronic component mounting area R1 in the first embodiment described above, the wall portion 33 may be formed around the inspection electrode disposing area R2. FIG. 7 is a bottom plan view of a circuit board 30B according to a first variation of the first embodiment of the disclosure.

In the circuit board 30B according to the first variation, the wall portion 33 is formed around the stepped portion 36. The wall portion 33 is formed on four sides of the stepped portion 36, whereby the imaging unit can be kept horizontal even when a load is applied to the proximal end side.

Figure 8:
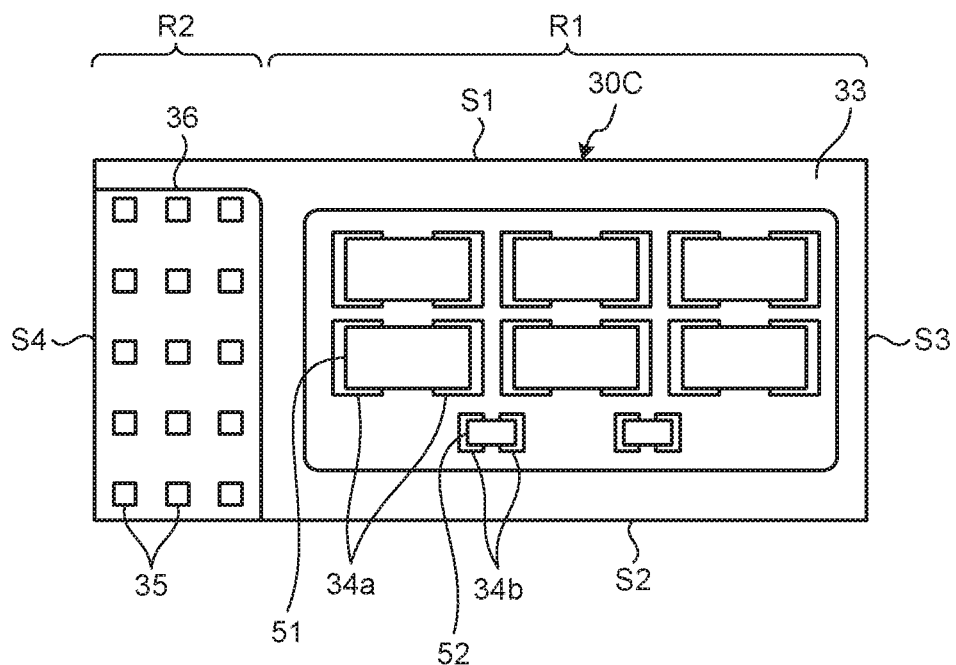
FIG. 8 is a bottom plan view of a circuit board according to a second variation of the first embodiment of the disclosure.
Figure 9:
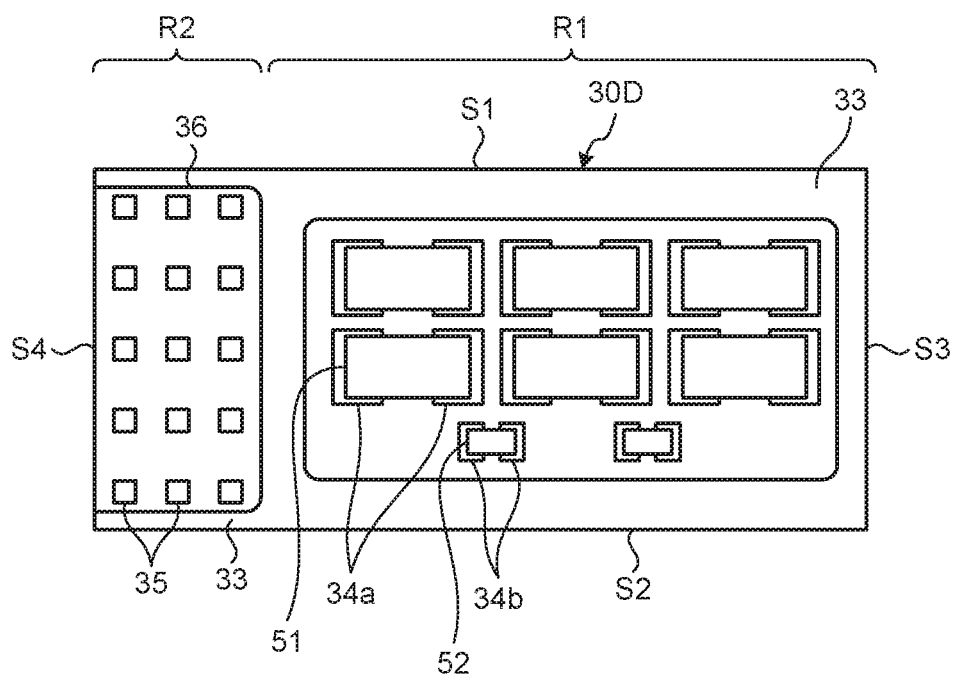
FIG. 9 is a bottom plan view of a circuit board according to a third variation of the first embodiment of the disclosure.

Here, although the wall portion 33 formed in the inspection electrode disposing area R2, is disposed on four sides of the inspection electrode disposing area R2 in the first variation, it is not limited thereto, and the wall portion 33 may be formed at least on two sides. FIG. 8 is a bottom plan view of a circuit board 30C according to a second variation of the first embodiment of the disclosure. FIG. 9 is a bottom plan view of a circuit board 30D according to a third variation of the first embodiment of the disclosure.

In the circuit board 30C according to the second variation, the wall portion 33 is formed on a side S1 and a side S3 around the stepped portion 36. Since the wall portion 33 is not formed on a side S4 and a side S2 in the second variation, filling of the sealing resin on the inspection electrode 35 can be easily performed from the side S4 or the side S2. The wall portion 33 may be formed on the side S2 and the side S3 around the stepped portion 36, or on the side S4 and the side S3.

Further, in the circuit board 30D according to the third variation, the wall portion 33 is formed around the stepped portion 36 except the side S4, that is, the sides S1, S2, and S3. Since the wall portion 33 is not formed on the side S4 in the third variation, the filling of the sealing resin on the inspection electrode 35 can be easily performed from the side S4. In addition, the imaging unit can be kept horizontal even when a load is applied to the proximal end side. The wall portion 33 may be formed on the sides S1, S3, and S4, or the sides S2, S3, and S4.

Figure 10:
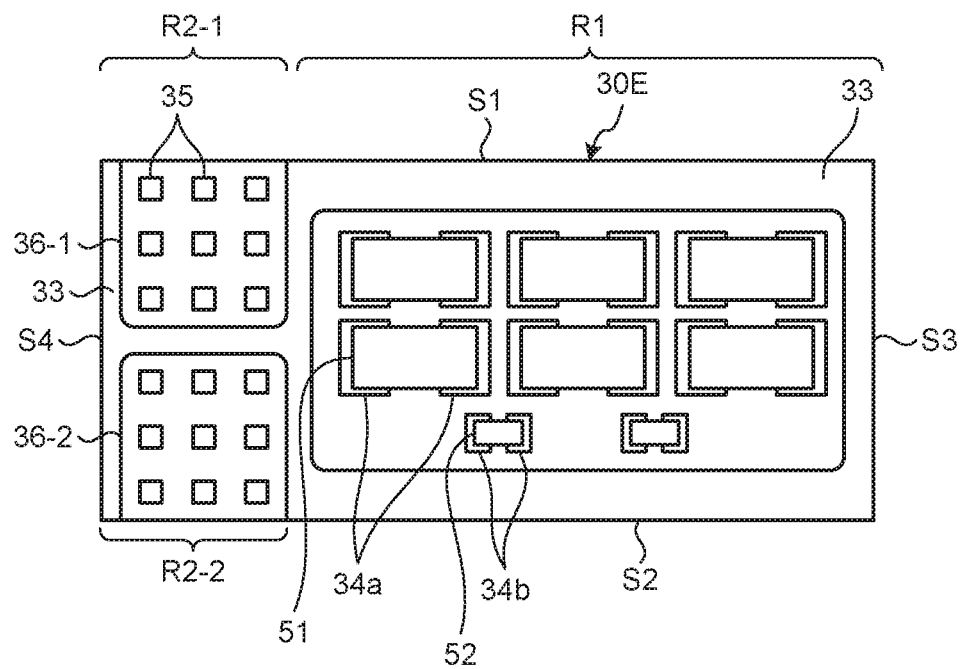
FIG. 10 is a bottom plan view of a circuit board according to a fourth variation of the first embodiment of the disclosure.

Furthermore, the inspection electrode disposing area R2 may be divided and disposed. FIG. 10 is a bottom plan view of a circuit board 30E according to a fourth variation of the first embodiment of the disclosure.

In the circuit board 30E according to the fourth variation, the inspection electrode disposing area R2 is divided by the wall portion 33 into a first inspection electrode disposing area R2-1 and a second inspection electrode disposing area R2-2. The wall portion 33 is formed on the sides S2, S3, and S4 around a stepped portion 36-1 in the first inspection electrode disposing area R2-1, and the wall portion 33 is formed on the sides S1, S3, and S4 around a stepped portion 36-2 in the second inspection electrode disposing area R2-2. Although the inspection electrode disposing area R2 is divided into two in the fourth variation, it is not limited thereto. The inspection electrode disposing area R2 may be divided into three or more, and may be divided for each inspection electrode 35.

Figure 11:
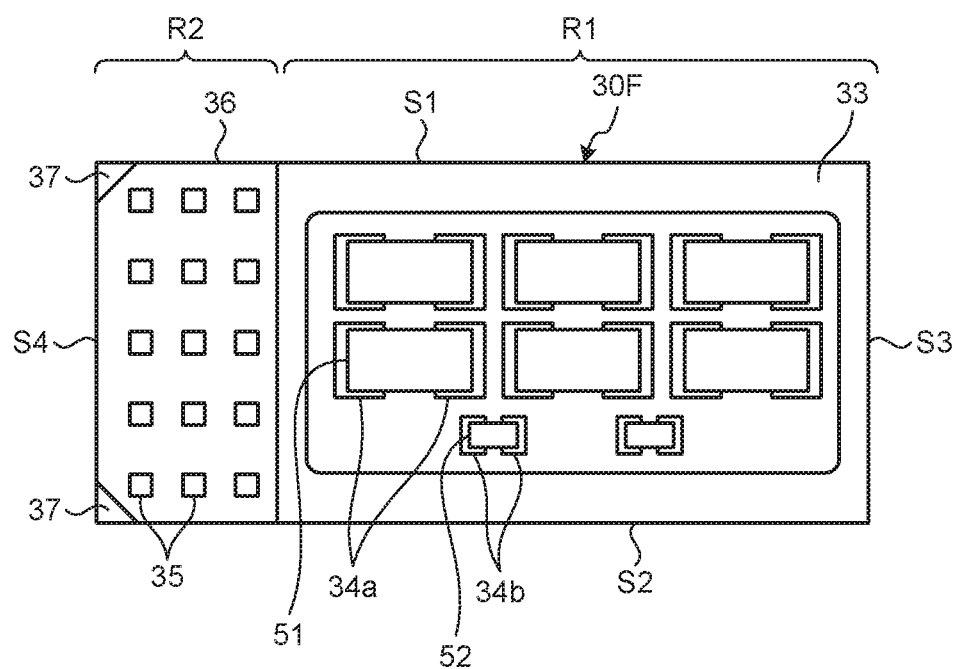
FIG. 11 is a bottom plan view of a circuit board according to a fifth variation of the first embodiment of the disclosure.

Furthermore, a pillar portion 37 may be disposed around the inspection electrode disposing area R2. FIG. 11 is a bottom plan view of a circuit board 30F according to a fifth variation of the first embodiment of the disclosure.

In the circuit board 30F according to the fifth variation, the pillar portion 37 is formed at a corner portion of the inspection electrode disposing area R2. A thickness of the circuit board 30F including the pillar portion 37 at the inspection electrode disposing area R2 (thickness of the circuit board 30F at the inspection electrode disposing area R2+height of the pillar portion 37) is set to be the same as a thickness of the circuit board 30F including the wall portion 33 formed in the electronic component mounting area R1, at the electronic component mounting area R1. Accordingly, the imaging unit can be kept horizontal even when a load is applied to the proximal end side, and the filling of the sealing resin on the inspection electrode 35 can be easily performed. Although the pillar portion 37 is in a triangular prism shape, it is not limited thereto, and may be in a prismatic shape. In addition, the pillar portion 37 may be disposed not only at the corner portion of the inspection electrode disposing area R2 but also around the inspection electrode disposing area R2 at regular intervals.

Figure 12:
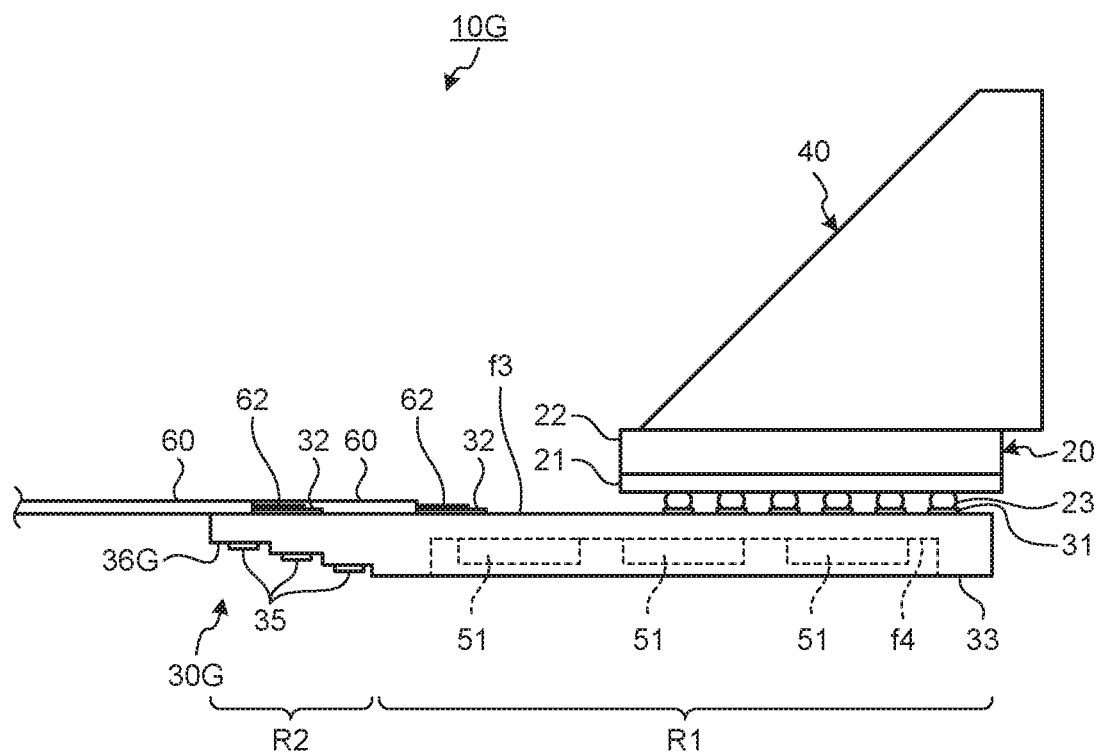
FIG. 12 is a side view of an imaging unit according to a sixth variation of the first embodiment of the disclosure.

Further, the stepped portion 36 is not limited to one step, and may be a plurality of steps. FIG. 12 is a side view of an imaging unit 10G according to a sixth variation of the first embodiment of the disclosure.

In a circuit board 30G according to the sixth variation, the inspection electrode disposing area R2 is formed of a stepwise stepped portion 36G including three steps. The stepped portion is not limited to the stepwise shape including a plurality of steps, and the plurality of steps may be concave or convex (in a side view).

Second Embodiment

Figure 13A:
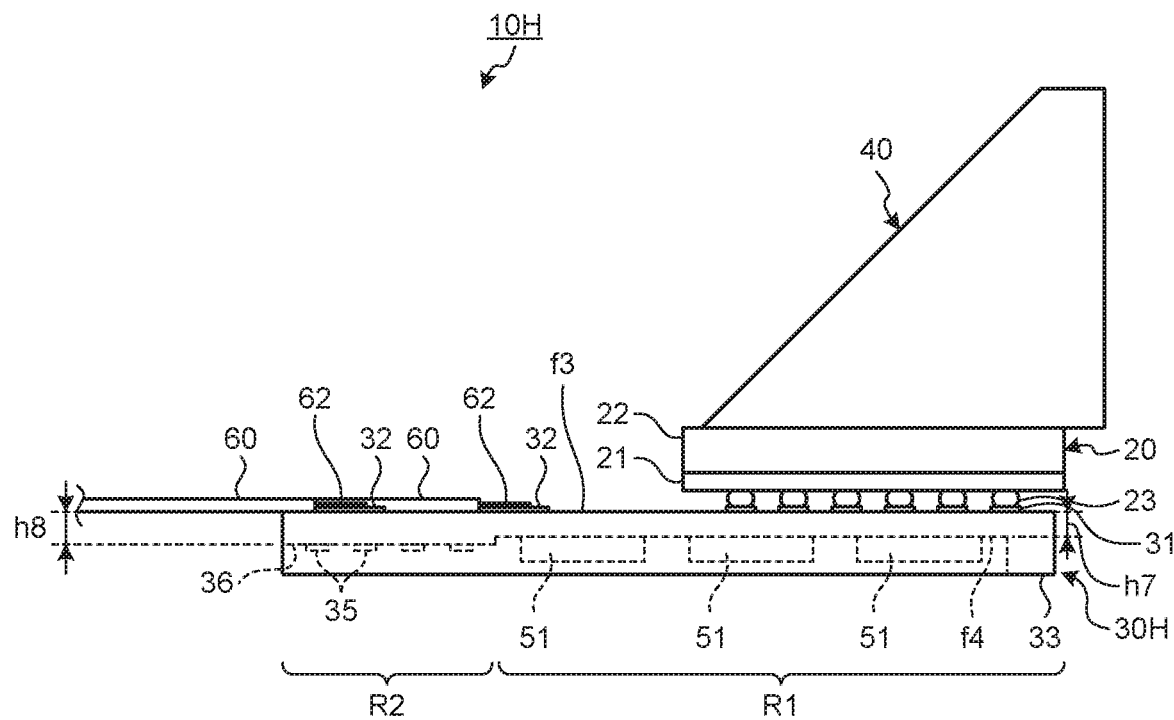
FIG. 13A is a side view of an imaging unit according to a second embodiment of the disclosure.
Figure 13B:
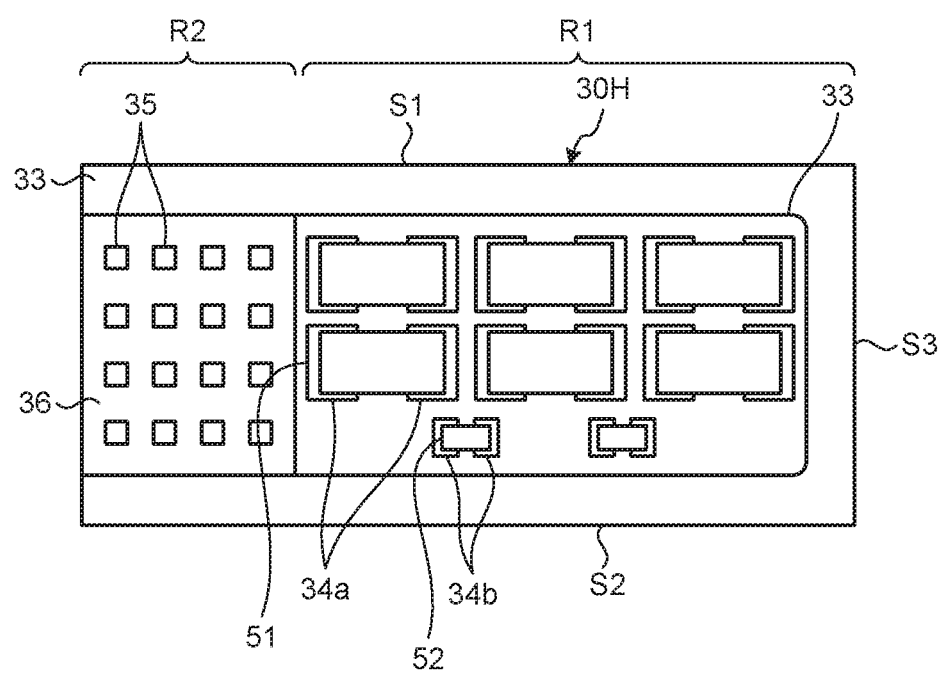
FIG. 13B is a bottom plan view of a circuit board according to the second embodiment of the disclosure.

In an imaging unit 10H according to a second embodiment, a wall portion 33 is disposed on three sides of an electronic component mounting area R1, and the wall portion 33 is formed on two facing sides of an inspection electrode disposing area R2. FIG. 13A is a side view of the imaging unit 10H according to the second embodiment of the disclosure. FIG. 13B is a bottom plan view of a circuit board 30H according to the second embodiment of the disclosure.

In the imaging unit 10H according to the second embodiment, the wall portion 33 is disposed on three sides around the electronic component mounting area R1, that is, a side S1, a side S2, and a side S3, the wall portion 33 is disposed on facing sides around the inspection electrode disposing area R2, that is, the side S1, and the side S2, and the wall portion 33 is not formed at a boundary between the electronic component mounting area R1 and the inspection electrode disposing area R2.

The electronic component mounting area R1 and the inspection electrode disposing area R2 are not flush with each other in the imaging unit 10H, and a thickness h8 of the circuit board 30H at the inspection electrode disposing area R2 is set to be thicker than a thickness h7 of the circuit board 30H at the electronic component mounting area R1. Accordingly, outflow of an underfill agent filled around electronic components 51 and 52 to the inspection electrode disposing area R2 can be prevented.

According to some embodiments, a maximum thickness of an inspection electrode disposing area in which an inspection electrode of a circuit board is formed is made thinner than a thickness of an electronic component mounting area including a wall portion formed in the electronic component mounting area so that the circuit board can be kept horizontal without using a special jig or the like, whereby an imaging unit and an endoscope excellent in accuracy can be produced.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging unit, comprising:
an optical system configured to collect light;
a semiconductor package including an image sensor provided on a front surface side of the semiconductor package and a sensor electrode provided on a back surface side of the semiconductor package, the image sensor being configured to receive light made incident from the optical system and perform a photoelectric conversion to generates an electric signal;
a plurality of electronic components; and
a circuit board including: a first connection electrode that is provided on a front surface side of the circuit board; and an electronic component mounting area and an inspection electrode disposing area that are provided on a back surface side of the circuit board, the first connection electrode being connected to the sensor electrode of the semiconductor package, the electronic component mounting area including a second connection electrode to which the plurality of electronic components is connected, the inspection electrode disposing area including an inspection electrode, wherein
a wall portion having a height higher than a height of the plurality of electronic components is formed at least on two facing sides around the electronic component mounting area, and a maximum thickness of the circuit board at the inspection electrode disposing area is thinner than a thickness of the circuit board including the wall portion, at the electronic component mounting area.

2. The imaging unit according to claim 1, wherein the wall portion is also formed around the inspection electrode disposing area.

3. The imaging unit according to claim 1, wherein a pillar portion is formed around the inspection electrode disposing area.

4. The imaging unit according to claim 1, wherein a thickness of the circuit board at the inspection electrode disposing area is thicker than a thickness of the circuit board at the electronic component mounting area.

5. An endoscope, comprising: an insertion portion provided with the imaging unit according to claim 1 at a distal end of the insertion portion.

* * * * *